United States Patent [19]

Hosaka et al.

[11] Patent Number: 5,684,173
[45] Date of Patent: *Nov. 4, 1997

[54] ORGANOSILICON COMPOUND AND ZIEGLER-NATTA CATALYST CONTAINING THE SAME

[75] Inventors: Motoki Hosaka; Kenji Goto, both of Chigasaki; Masahiko Matsuo, Koga-gun, all of Japan

[73] Assignee: Toho Titanium Co., Ltd., Chigasaki, Japan

[*] Notice: The term of this patent shall not extend beyond the expiration date of Pat. No. 5,494,872.

[21] Appl. No.: 380,980

[22] Filed: Jan. 31, 1995

Related U.S. Application Data

[63] Continuation-in-part of Ser. No. 309,885, Sep. 20, 1994, Pat. No. 5,498,770.

[30] Foreign Application Priority Data

Apr. 28, 1994 [JP] Japan .................................. 6-113754
Nov. 18, 1994 [JP] Japan .................................. 6-309962

[51] Int. Cl.⁶ .................................................... C07F 7/18
[52] U.S. Cl. ................... 556/482; 502/116; 502/125; 526/125.3
[58] Field of Search ............................................. 556/482

[56] References Cited

U.S. PATENT DOCUMENTS

| 4,906,695 | 3/1990 | Blizzard et al. ........................ 525/100 |
| 4,977,291 | 12/1990 | Gementi et al. ........................ 556/466 |
| 5,175,332 | 12/1992 | Chatterton et al. ..................... 556/482 |
| 5,248,803 | 9/1993 | Aoki et al. ............................... 556/482 |
| 5,308,818 | 5/1994 | Shamshonm et al. .................. 502/127 |
| 5,494,872 | 2/1996 | Hosaka et al. .......................... 502/115 |
| 5,498,770 | 3/1996 | Hosaka et al. .......................... 502/116 |

OTHER PUBLICATIONS

Caplus Accession No. 1995:417454 (1995).

Primary Examiner—Romulo H. Delmendo
Attorney, Agent, or Firm—Oblon, Spivak, McClelland, Maier & Neustadt, P.C.

[57] ABSTRACT

An organosilicon compound represented by formula (I)

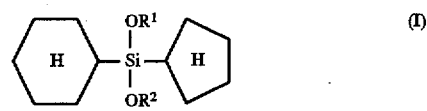

wherein $R^1$ and $R^2$ which may be the same or different, each represents an alkyl group having 1 to 3 carbon atoms. The organosilicon compound is used as en effective electron donor ingredient of a Ziegler-Natta catalyst for olefin polymerization.

1 Claim, 3 Drawing Sheets

ORGANOSILICON COMPOUND AND ZIEGLER-NATTA CATALYST CONTAINING THE SAME

This is a continuation-in-part of application Ser. No. 08/309,885 filed Sep. 20, 1994, now U.S. Pat. No. 5,498,770.

FIELD OF THE INVENTION

The present invention relates to a novel organosilicon compound usable as a silane coupling agent or as a component of an olefin polymerization catalyst. The present invention also relates to a Ziegler-Natta catalyst for olefin polymerization, which contains the organosilicon compound as an effective electron doner ingredient.

BACKGROUND OF THE INVENTION

Hitherto, a large number of specific organosilicon compounds for use as an electron donor (external electron donor) as a component of a Ziegler-Natta catalyst or for use as an electron donor (internal electron donor) contained in a solid catalyst component of a Ziegler-Natta catalyst have been proposed for the purpose of producing polymers having improved stereoregularity or enhancing catalytic activity in olefin polymerization using the catalyst.

Various proposals have been made on processes for producing this kind of organosilicon compounds. For example, U.S. Pat. No. 4,977,291 proposes a process for producing a silicon compound having at least one cycloalkyl group in which a silicon compound containing an aromatic group as a starting compound is hydrogenated in the presence of a catalyst, e.g., a Raney nickel catalyst.

U.S. Pat. No. 4,958,041 discloses a process for producing a diorganodialkoxysilane having at least one branched alkyl group other than the two alkoxy groups in which a tetraalkoxysilane or a monoorganotrialkoxysilane is reacted with a Grignard reagent having the structural formula RMgX wherein R is an alkyl group or a cycloalkyl group and X is a halogen atom.

In JP-A-5-255350 is disclosed a cycloalkoxysilane represented by the formula $(R'O)_x(R')_ySi(OR)_{4-x-y}$ for use as an electron donor component of a Ziegler-Natta catalyst for olefin polymerization, wherein each R is independently selected from alkyl groups having 1 to 5 carbon atoms and acyl groups having 2 to 5 carbon atoms, each R' is independently selected from a cyclopentyl group, a cyclohexyl group, a cycloheptyl group, and substituted groups thereof, x is 1, 2, 3, or 4, and y is 0, 1, or 2. The term "JP-A" as used herein means an "unexamined published Japanese patent application." JP-A-5-310757 discloses tert-butoxycyclopentyldiethoxysilane as a novel silane compound and a process for producing the same.

On the other hand, examples of conventional olefin polymerization techniques employing a Ziegler-Natta catalyst containing an organosilicon compound as one component thereof include the method disclosed in JP-A-57-63310 and JP-A-57-63311 in which method a catalyst comprising a combination of (i) a solid catalyst component composed of a magnesium compound, a titanium compound and an internal electron donor, (ii) an organoaluminum compound, and (iii) an organosilicon compound having an Si-O-C bond as an external electron doner is used to polymerize an olefin having 3 or more carbon atoms. However, this method is not always satisfactory in obtaining a highly stereoregular polymer in high yield, so that a further improvement has been desired.

Under these circumstances, JP-A-2-84404 proposes an olefin polymerization catalyst comprising (i) a solid titanium catalyst component composed of magnesium, titanium and a halogen as essential ingredients formed by contacting a magnesium compound with a titanium compound, (ii) an organoaluminum compound, and (iii) an organosilicon compound having a cyclopentyl, cyclopentenyl, or cyclopentadienyl group or a derivative thereof, and further proposes a method for polymerizing or copolymerizing olefins in the presence of the catalyst. This technique is to enhance a catalyst activity to such a degree as to enable the omission of the so-called deashing step for removing a catalyst residue including chlorine and titanium from the produced polymer, and also to improve the yield of a stereoregular polymer and enable such a high catalytic activity to last over long. This technique has succeeded in achieving these purposes.

When the olefin polymerization catalysts containing the organosilicon compounds disclosed in the above-mentioned references as internal or external electron doner are used for olefin polymerization, however, the resulting polymer has a narrower molecular weight distribution than polymers produced by polymerization using a conventional olefin polymerization catalyst comprising a titanium trichloride catalyst component and an organoaluminum compound and optionally containing another electron donor as the third component. Such a polyolefin having a narrow molecular weight distribution has impaired moldability, so that applications of the final polyolefin products obtained therefrom are limited. If the conventional catalyst is used in an attempt to obtain a polyolefin having a broad molecular weight distribution, on the other hand, it results in reduced yield of highly stereoregular polymer.

A weight reduction in plastics for use in motorcars, electrical appliances, etc. is strongly desired for the purpose of energy or resource saving in relation to recent global environmental problems. For attaining this desire, it is necessary to reduce the thickness of a molding while maintaining its strength including impact resistance. This can, for example, be attained by improving the crystallinity of a resin to thereby improve the rigidity thereof. Therefore, it has been desired to develop a polyolefin production catalyst with which a polymer having not only improved crystallinity but also a broadened molecular weight distribution can be obtained.

SUMMARY OF THE INVENTION

An object of the present invention is to provide a novel organosilicon compound extremely useful as a component of a catalyst, in particular a catalyst for the polymerization of an olefin such as propylene or ethylene, with which catalyst a polymer having a broad molecular weight distribution and high crystallinity can be obtained while maintaining especially high catalytic activity and an extremely high yield of highly stereoregular polymer.

Another object of the present invention is to provide a Ziegler-Natta catalyst for olefin polymerization which comprises the organosilicon compound as an effective electron donor ingredient.

As a result of extensive studies on olefin polymerization catalysts in order to overcome such problems of conventional techniques, the present inventors have succeeded in developing a novel organosilicon compound which is usable as an internal and/or external electron donor serving as a component of an olefin polymerization catalyst, and they have ascertained that the organosilicon compound is extremely effective. That is, the above objects are accomplished with an organosilicon compound represented by formula (I)

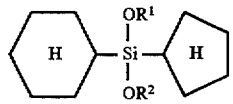 (I)

wherein $R^1$ and $R^2$, which may be the same or different, each represents an alkyl group having 1 to 3 carbon atoms.

DETAILED DESCRIPTION OF THE INVENTION

Figure 1:
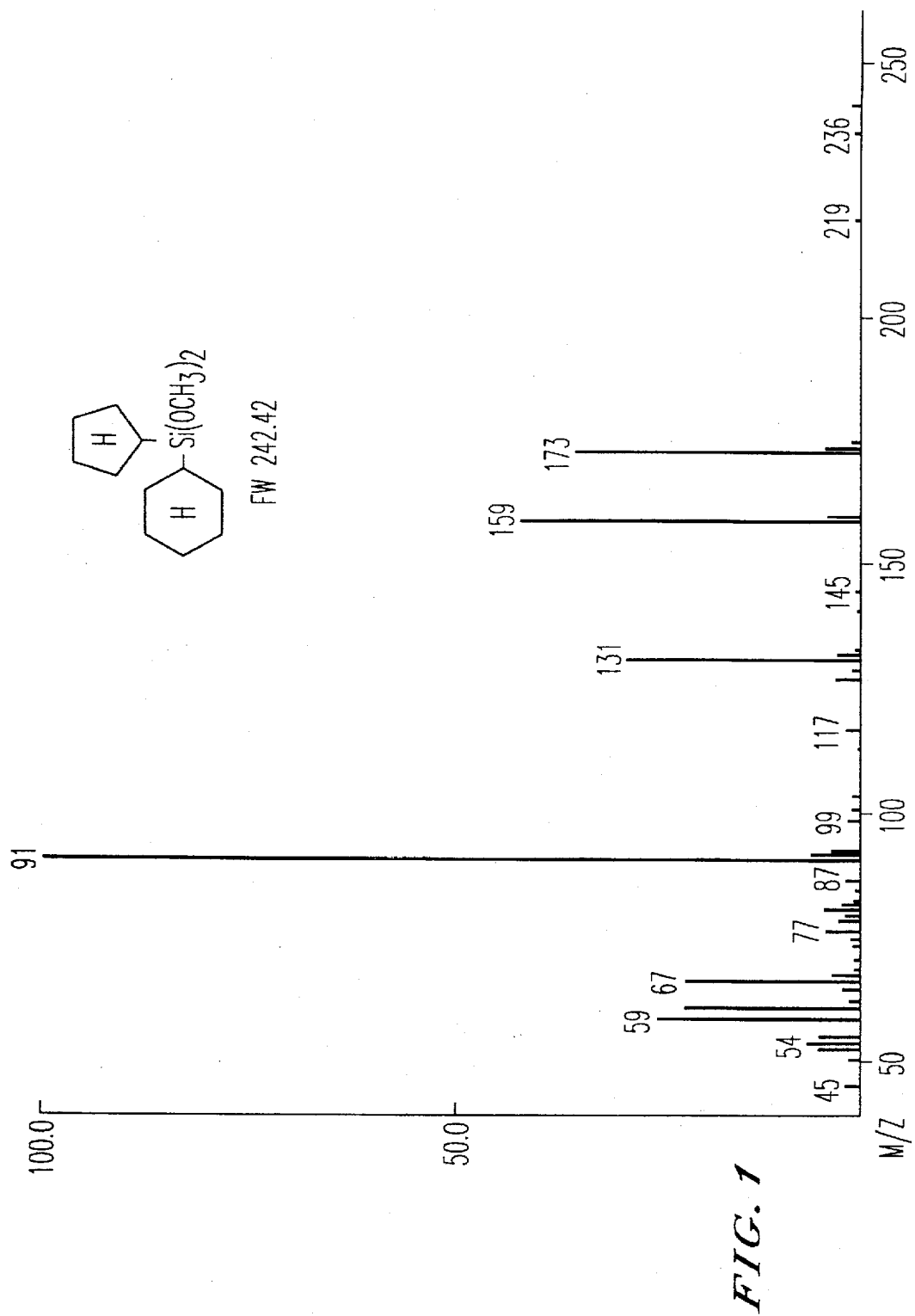
FIG. 1 is a chart showing the results of MS with which cyclohexylcyclopentyldimethoxysilane was identified.

Examples of the alkyl group for $R^1$ and $R^2$ in formula (I) include methyl, ethyl, n-propyl, and isopropyl. Of these, methyl and ethyl are preferred.

The organosilicon compound of the present invention, which is represented by formula (I) described above, is a cyclohexylcyclopentyldialkoxysilane. Examples of the cyclohexylcyclopentyldialkoxysilane include cyclohexylcyclopentyldimethoxysilane, cyclohexylcyclopentyldiethoxysilane, cyclohexylcyclopentyldi-n-propoxysilane, and cyclohexylcyclopentyldiisopropoxysilane. Of these, cyclohexylcyclopentyldimethoxysilane and cyclohexylcyclopentyldiethoxysilane are preferred organosilicon compounds for use as an electron donor serving as a component of an olefin polymerization catalyst.

The organosilicon compound of the present invention is useful as an (internal and/or external) electron donor for various olefin polymerization catalysts. Namely, the organosilicon compound can be used as an electron donor in the homo- or copolymerization of ethylene, propylene, 1-butene, 1-pentene, 4-methyl-1-pentene, vinylcyclohexane, etc. In particular, the organosilicon compound is suitable for use as an electron donor of a catalyst for the homopolymerization of ethylene or propylene or the copolymerization of ethylene and propylene, and the optimal use thereof is as an electron donor of a catalyst for the homopolymerization of propylene or the copolymerization of propylene and ethylene.

The cyclohexylcyclopentyldialkoxysilane of the present invention can be prepared by various methods. In one of the simplest methods, the organosilicon compound is obtained by the reaction of a monocycloalkyltrialkoxysilane (i.e., monocyclohexyl- or monocyclopentyl-trialkoxysilane) with a cycloalkyl Grignard reagent (i.e., a Grignard reagent having a cyclopentyl or cyclohexyl group, respectively).

For example, cyclopentyl chloride (commercial product) is first reacted with magnesium in the presence of a solvent, e.g., an ether such as tetrahydrofuran, diethyl ether, or di-n-butyl ether, to yield a cyclopentyl Grignard reagent (cyclopentylmagnesium chloride). This reaction may be carried out at a temperature of from room temperature to 60° C. The cyclopentyl Grignard reagent is then reacted with cyclohexyltrimethoxysilane to obtain cyclohexylcyclopentyldimethoxysilane; this reaction may be conducted in the presence of an ether such as tetrahydrofuran, diethyl ether, or di-n-butyl ether as in the above-described first reaction, or in the presence of an aliphatic hydrocarbon solvent such as hexane or heptane or an aromatic hydrocarbon solvent such as toluene, benzene, or xylene. This reaction may be carried out at a temperature of from 50° C. to 200° C., preferably at a temperature of from 100° C. to 200° C or at a temperature of from 100° C. to 200° C. under boiling or refluxing of the solvent.

Although the monocycloalkyltrialkoxysilane, e.g., cyclohexyltrimethoxysilane employed above, for use in the above reaction may be a commercial product, it may be prepared by various known methods. In one method, the desired compound is prepared by reacting cyclohexyltrichlorosilane with methanol to alkoxylate the silane compound with the evolution of hydrogen chloride. Although the cyclohexyltrichlorosilane for use in this reaction may be a commercial product, it may be easily prepared by the hydrosilylation reaction of cyclohexene with trichlorosilane ($HSiCl_3$). Another method for preparing cyclohexyltrimethoxysilane comprises hydrogenating a commercial product of phenyltrimethoxysilane in the presence of a catalyst, e.g., a Raney nickel catalyst.

The cyclohexylcyclopentyldimethoxysilane thus produced can be identified by nuclear magnetic resonance spectroscopy ($^1$H-NMR, $^{13}$C-NMR), infrared absorption spectrometry (IR), mass spectrometry (MS), etc. $^{13}$C-NMR spectrometry (in $CDCl_3$) gives a spectrum which has a signal at $\delta=50.7$ attributable to the carbon atoms of the methoxy groups, signals at $\delta=24.5$, 26.8, 26.9, and 27.8 attributable to the cyclohexyl group, and signals at $\delta=22.8$, 26.7, and 27.4 attributable to the cyclopentyl group. IR spectrometry gives a spectrum having a peak at around 1,100 $cm^{-1}$ attributable to the Si-O-C bonds.

The organosilicon compound of the present invention, i.e., a cyclohexylcyclopentyldialkoxysilane, when used as an electron donor serving as one component of a Ziegler-Natta catalyst for olefin polymerization, makes it possible to obtain a polyolefin having a broad molecular weight distribution and high crystallinity while retaining high performances with respect to catalytic activity and the yield of highly stereoregular polymer which performances are not lower than those conventionally known as high-performance catalysts.

The Ziegler-Natta catalyst of the present invention is not particularly limited as long as the organosilicon compound of formula (I) is contained as an internal or external electron doner, and any conventional components for the Ziegler-Natta catalyst can be used together with the organosilicon compound. In a preferred embodiment of the present invention, the Ziegler-Natta catalyst comprises (A) a solid catalyst component essentially containing magnesium, titanium, an electron donor compound, and a halogen which is prepared by contacting a magnesium compound, a titaniumhalide compound, and an internal electron donor compound, (B) an organoaluminum compound, and (C) the organosilicon compound of formula (I).

Solid catalyst component (A) can be prepared by contacting the above-mentioned magnesium compound, titanium halide compound and electron donor compound in a manner appropriately selected from conventional means. Known methods for preparing a solid catalyst component are disclosed, e.g., in JP-A-63-308004, JP-A-63-314211, JP-A-64-6006, JP-A-64-14210, JP-A-64-43506, JP-A-63-3010, and JP-A-62-158704.

Examples of organoaluminum compound (B) are triethylaluminum, diethylaluminum chloride, triisobutylaluminum, diethylaluminumbromide, and diethylaluminumhydride. These organoaluminum compounds may be used either individually or in combination of two or more thereof. Preferred of them are triethylaluminum and triisobutylaluminum.

In the present invention, an olefin is homo- or copolymerized in the presence of the Ziegler-Natta catalyst comprising solid catalyst component (A), organoaluminum compound (B), and organosilicon compound (C). The ratio of components (A), (B), and (C) to be used is not particularly limited as long as the effects of the present invention are not impaired. Usually, organoaluminum compound (B) is used in an amount of from 1 to 500 mol and preferably from 5 to 400 mol per mol of the titanium atom in solid catalyst component (A), and organosilicon compound (C) is used in an amount of from 0.0020 to 2 mol and preferably from 0.0025 to 0.5 mol per mol of organoaluminium compound (B).

The Ziegler-Natta catalyst of the present invention can be prepared by bringing the above-described components (A), (B) and (C) into contact. There is no particular limitation on the order in contact of the components (A), (B) and (C). In general, the component (B) is brought into contact with the component (C) and subsequently with the component (A), or the component (B) is brought into contact with the component (A) and subsequently with the component (C).

The present invention will be explained below in more detail by reference to the following Examples. A process for preparing a cyclohexylcyclopentyldialkoxysilane is described in detail in Example 1, but this process is a mere example and should not be construed as limiting the scope of the invention. Example 2 is given in order to demonstrate the usefulness of the organosilicon compound of the present invention as an electron donor of a Ziegler-Natta catalyst for olefin polymerization, but the applications of the organosilicon compound of the invention are not limited thereto.

EXAMPLE 1

Into a 2-liter four-necked flask equipped with a stirrer, thermometer, Dimroth condenser, and dropping funnel was introduced 18.5 g (0.76 mol) of magnesium shavings. The magnesium was dried in an argon stream, and 20 ml of di-n-butyl ether was then added thereto. The contents were cooled to room temperature, and a small amount of 1,2-dibromoethane was added thereto to activate the magnesium. A solution prepared by dissolving 79.6 g (0.76 mol) of cyclopentyl chloride in 600 ml of di-n-butyl ether was then added dropwise over a period of 3.5 hours, during which the temperature of the system spontaneously increased to 50° C. Subsequently, 143.0 g (0.70 mol) of cyclohexyltrimethoxysilane was added thereto at room temperature, and the reaction was then conducted for 1 hour under reflux.

Figure 2:
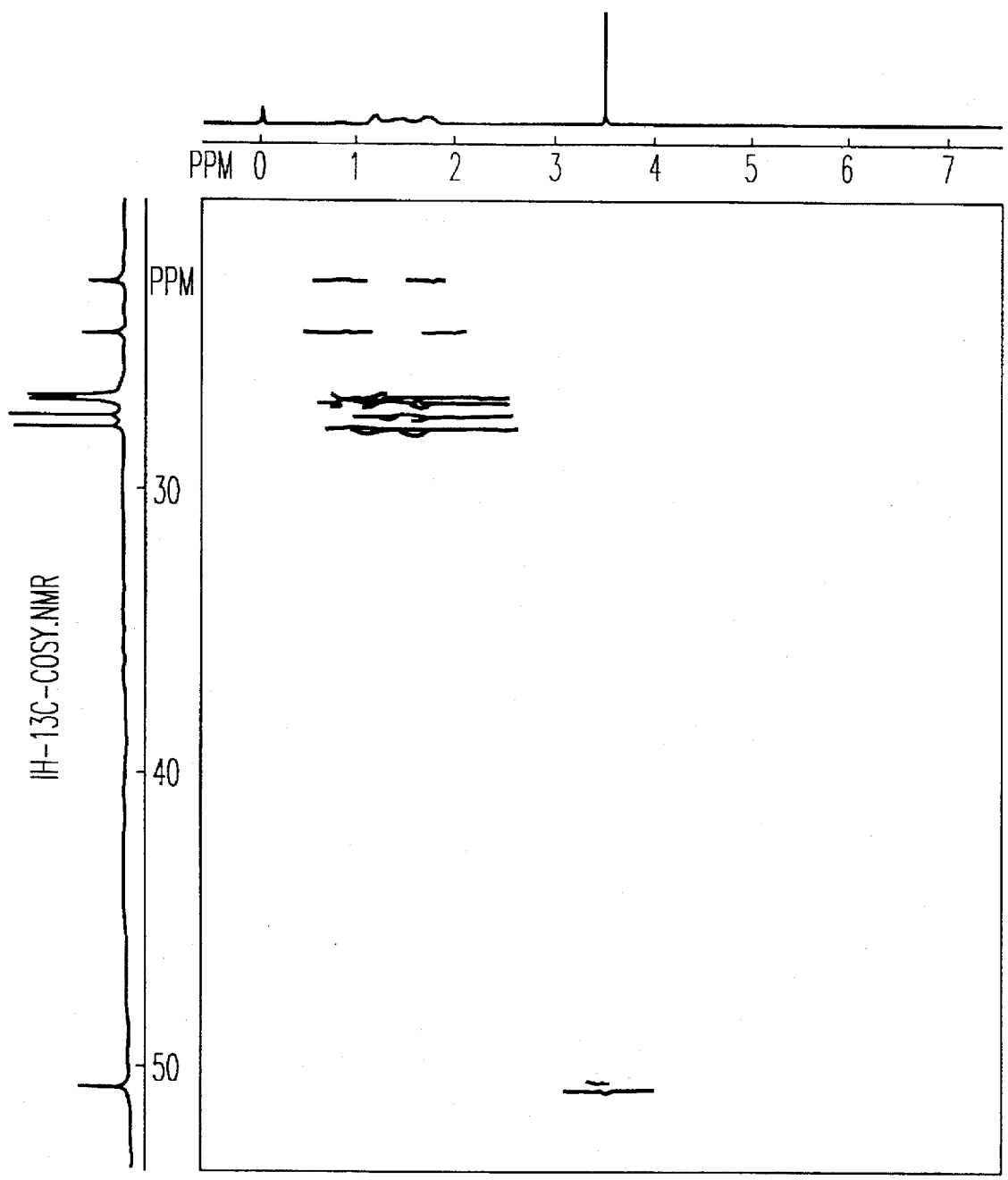
FIG. 2 is a chart showing the results of two-dimensional analysis by $^1$H-NMR/$^{13}$C-NMR (COSY spectrum) with which cyclohexylcyclopentyldimethoxysilane was identified.
Figure 3:
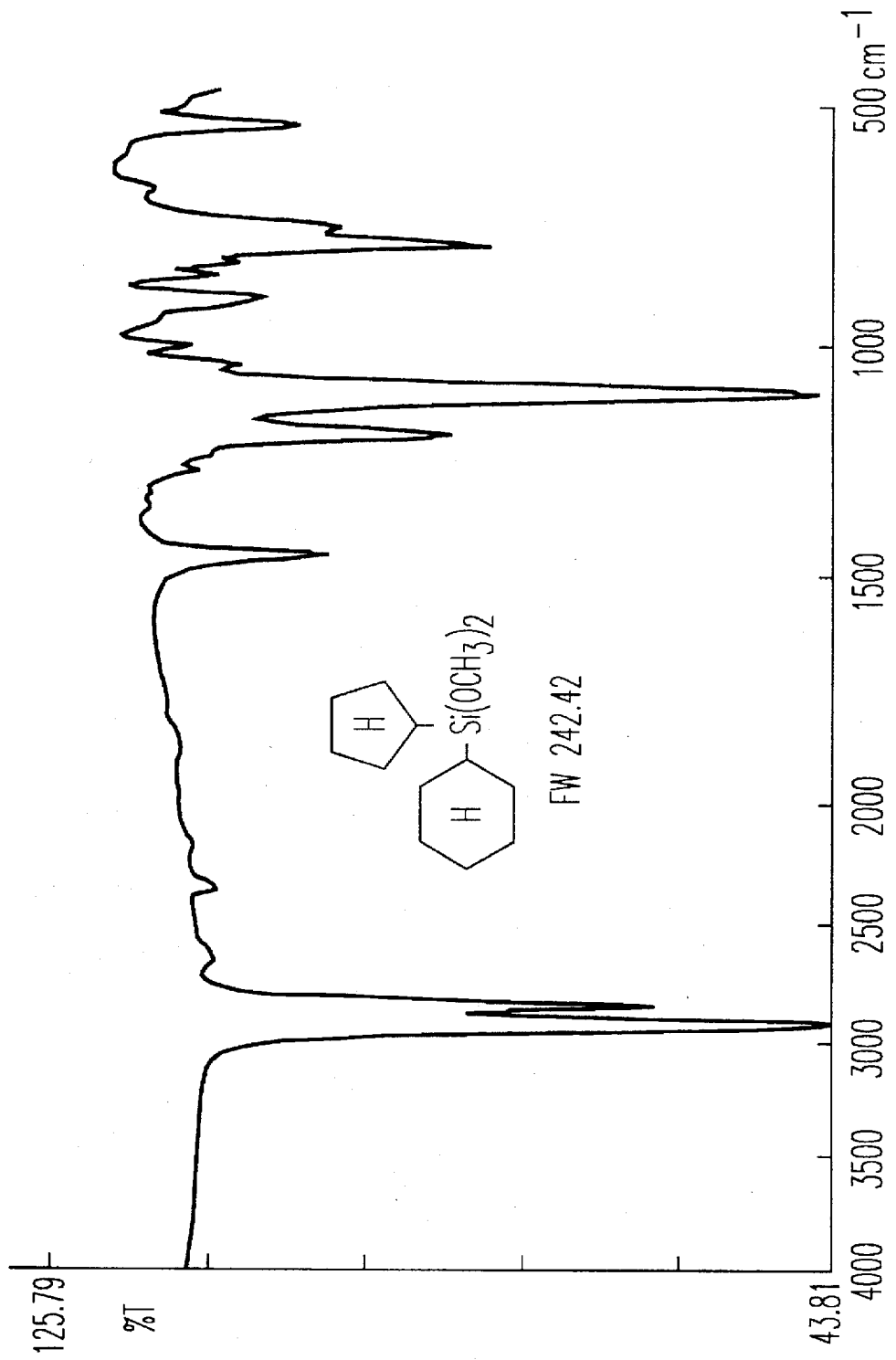
FIG. 3 is a chart showing the results of IR with which cyclohexylcyclopentyldimethoxysilane was identified.

After completion of the reaction, the reaction mixture was cooled to room temperature, and 372 g (0.38 mol) of a 10% aqueous sulfuric acid solution was added thereto dropwise at a temperature of 40° C. or lower. The organic layer was washed with 300 ml of a 1% aqueous sodium hydrogen carbonate solution and then dried over anhydrous magnesium sulfate. After the drying agent was filtered off, vacuum distillation was performed to obtain 143.6 g of a fraction having a boiling point of 78° C. at 0.2 Torr. The yield was 84.6%. This reaction product was ascertained to be cyclohexylcyclopentyldimethoxysilane by MS, two-dimensional analysis with $^1$H-NMR/$^{13}$C-NMR, and IR. The results of MS, $^1$H-NMR/$^{13}$C-NMR (COSY spectrum), and IR are shown in FIGS. 1, 2, and 3, respectively.

The analyses by MS, $^1$H-NMR/$^{13}$C-NMR, and IR were carried out under the following conditions.

MS: apparatus . . . Finigan Mat (GC-MS).
$^1$H-NMR/$^{13}$C-NMR: apparatus . . . JEOL GSX270, solvent . . . CDCl$_3$.
IR: apparatus . . . Perkin Elmer 1600 Series (FT-IR), KBr sand method.

EXAMPLE 2

Preparation of Solid Catalyst Component:

Into a 200-ml round-bottom flask the inside atmosphere of which had been sufficiently replaced with nitrogen gas and which was equipped with a stirrer were introduced 10 g of diethoxymagnesium and 80 ml of toluene. The contents were stirred to obtain a suspension. To this suspension was added 20 ml of titanium tetrachloride. The mixture was heated and, at the time when the temperature thereof had reached 62° C., 1.0 ml of diethyl phthalate was added. This mixture was then heated and, at the time when the temperature thereof had reached 110° C., 3.5 ml of dioctyl phthalate was added. The resulting mixture was heated to 112° C. and stirred at this temperature for 1.5 hours to allow a reaction to proceed. After completion of the reaction, the reaction product was washed twice with 100 ml of toluene heated at 90° C. To the washed reaction product were added 20 ml of titanium tetrachloride and 80 ml of toluene. This mixture was heated to 100° C. and stirred for 2 hours to allow a reaction to proceed. After completion of the reaction, the reaction product was washed 10 times with 100 ml of n-heptane warmed at 40° C. to obtain a solid catalyst component. The titanium content of this solid catalyst component was measured and found to be 2.46% by weight.

Formation of Polymerization Catalyst and Polymerization of Olefin:

Into a 2.0-liter autoclave the inside atmosphere of which had been sufficiently replaced with nitrogen gas and which was equipped with a stirrer were introduced 1.32 mmol of triethylaluminum, 0.13 mmol of cyclohexylcyclopentyldimethoxysilane, and 0.0066 mmol of the solid catalyst component in terms of the amount of titanium atoms. Thus, a polymerization catalyst was formed. Thereafter, 1.8 liters of hydrogen gas and 1.4 liters of liquefied propylene were introduced into the autoclave to conduct polymerization at 70° C. for 30 minutes. The weight (a) of the polymer thus obtained was 349.1 g. When this polymer was extracted with boiled n-heptane for 6 hours, the n-heptane-insoluble amount (b) was 343.2 g. The catalytic activity was 23,900 g per g of the solid catalyst component used. The yield of the wholly crystalline polymer was 98.3%. The polymer yielded had an MI of 3.6 g/10-min, a molecular weight distribution of 7.1, and a melting point of 164.0° C.

The catalytic activity per unit weight of the solid catalyst component used was calculated using the following equation.

$$\text{Catalytic Activity} = \frac{(a)\,(g)}{\text{Solid Catalyst Component}\,(g)}$$

The yield of wholly crystalline polymer was calculated using the following equation.

$$\text{Yield of Wholly Crystalline Polymer} = \frac{(b)}{(a)} \times 100 \, (\%)$$

The molecular weight distribution was determined using the following equation.

$$\text{Molecular Weight Distribution} = \frac{\text{Weight-average Molecular Weight } (M_w)}{\text{Number-average Molecular Weight } (M_n)}$$

As described above, the organosilicon compound of the present invention, when used as an electron donor serving as one component of an olefin polymerization catalyst, gives a polyolefin having a broad molecular weight distribution and high crystallinity, while retaining high performances with respect to catalytic activity and the yield of highly stereo-regular polymer which performances are equal to or higher than those of conventionally known high-performance catalysts. The organosilicon compound therefore is capable of providing at low cost a general-purpose polyolefin excellent in rigidity and moldability. Furthermore, the organosilicon compound of the present invention is expected to be useful as, e.g., a silane coupling agent, a modifier for resins, etc.

While the invention has been described in detail and with reference to specific embodiments thereof, it will be apparent to one skilled in the art that various changes and modifications can be made therein without departing from the spirit and scope thereof.

What is claimed is:

1. Cyclohexylcyclopentyldimethoxysilane.

* * * * *